US00PP09896P

United States Patent [19]

Roberson

[11] Patent Number: Plant 9,896

[45] Date of Patent: May 20, 1997

[54] CANNA PLANT NAMED 'ROBLIBSCA'

[76] Inventor: Robert J. Roberson, 31706 E. Pink Hill Rd., Grain Valley, Jackson County, Mo. 64029

[21] Appl. No.: 576,341

[22] Filed: Dec. 21, 1995

[51] Int. Cl.[6] ..... A01H 5/00

[52] U.S. Cl. ..... Plt./68.1

[58] Field of Search ..... Plt./68.1

*Primary Examiner*—Howard J. Locker

*Attorney, Agent, or Firm*—Rothwell, Figg, Ernst & Kurz pc

[57] ABSTRACT

A new cultivar of Canna is provided. The dwarf height with overall compact growth characteristics, a multiplication rate of eight to twenty-five plants per growing season, an inflorescence with blooms of scarlet red accented by darker scarlet splashes, contrasting burgundy foliage and strong winter storage capability providing a cultivar well suited for garden or pot plant having no unusual susceptibility to the traditional Canna diseases and insects.

1 Drawing Sheet

SUMMARY OF THE INVENTION

This invention relates to a new and distinct Canna cultivar which is outstanding because of its dwarf height, with overall compact growth characteristics, a multiplication rate of eight to twenty-five plants per growing season, deep scarlet red flowers which shed spent blooms quickly, good winter storage capability, low tendency to set seed, and primarily selected for those characteristics. This selection was made from a specially designed Canna hybridizing program with said hybrid cultivars being planted and grown in Grain Valley, Mo.

ORIGIN AND ASEXUAL REPRODUCTION

Asexual reproduction of this cultivar by dividing the rhizome was directed by me, such reproduction establishing that the plant does in fact maintain the characteristics described, in successive generations.

It should be noted that the plant was initially selected from a Canna planting being grown near Grain Valley, Mo. in a cultivated area and has since been reproduced by dividing the rhizomes in the vicinity of Grain Valley, Mo. with the new and distinct characteristics stated herein, found to be maintained through successive generations as before recited.

*Canna generalis* is a group of tropical to sub-tropical herbaceous plants grown primarily for their rapid growth and vivid, flamboyant, summer blooms. They are grown in USDA zones 9–10 as a perennial and in USDA zones 3–8 as an annual. General growth habit includes an erect central (main) stalk with large tropical alternate leaves. This massive plant, usually 158 cm–211 cm in height, is topped by a colorful, inflorescent display. They are of easy cultivation in any fertile, moist soil, especially soils high in humus.

The cultivar of *Canna generalis* "Roblibsca" may further be described as having a number of distinctive characteristics which are enumerated in the succeeding specific description but broadly stated as comprising a dwarf height (50 cm–62 cm), with overall compact growth characteristics and a multiplication rate of eight to twelve plants in zone 5 and as high as 25 in zone 9 per growing season. The floral display has flowers of scarlet red (PMS#186) with small irregular splashes of deeper scarlet (PMS#187). The bloom period begins at approximately twelve (12) weeks after planting and continues until frost.

I have chosen to identify this new cultivar as *Canna generalis* "Roblibsca". It is possible that other identification will be adopted in the trade, but the name selected will serve for purposes hereof.

BRIEF DESCRIPTION OF THE DRAWING

The accompanying photograph shows as nearly true as it is reasonably possible to make the same, in a color illustration of this character, typical flowers and leaves of the new variety. The photographic drawing illustrates the flower form, the novel and distinctive scarlet flowers, and the striated burgundy foliage.

In the photograph.

DETAILED DESCRIPTION

Figure 1:
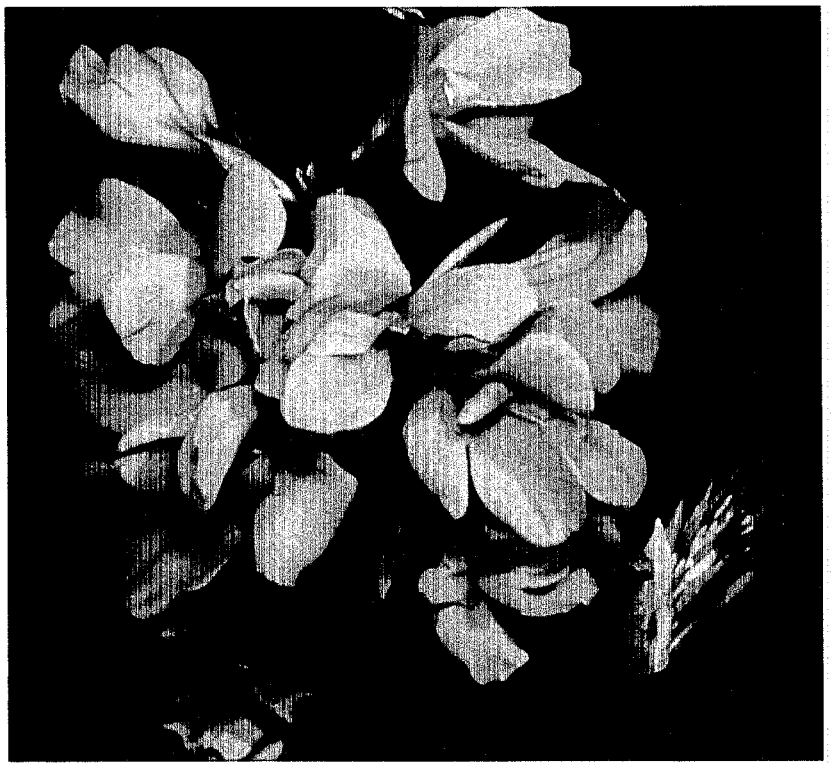
FIG. 1 illustrates the mature flower.

In order to more specifically identify the cultivar, descriptive details are set forth hereinafter, along with related aspects of the plant which serve to distinguish the same, all colors being noted as compared with the Pantone Matching System (PMS). The measurements and colors were recorded from mature plants grown in the vicinity of Grain Valley, Mo., unless stated otherwise.

Parentage:

*Seed parent.*—*Canna generalis* hybrid (Roberson Sdlg.#LR91-1).

*Pollen parent.*—Self pollinated.

Propagation: Asexual reproduction by rhizome division started near Grain Valley, Mo.

PLANT DESCRIPTIONS

*Inflorescence and reproductive parts:* The overall inflorescence is thyrsoid (mixed) and is approximately 21 cm in length by 13 cm in width when mature. The terminal axis is indeterminate and the lateral axis are cymose and determinate. The large, zygomorphic, hermaphrodite flowers are borne terminally and more or less erect in a racemose inflorescence and are at anthesis together with one that is in bud. The flowers, borne on short pedicels occur in pairs forming a two-flowered cincinnus. Each flower is substended by a bract. The outer whorl of the perianth consists of three free, imbricate sepals, the inner whorl of three basically united petals. There are typically three to five petaloid staminodes (showy portion of inflorescence) with the smaller fertile petaloid stamen and style visible at the center of the flower. Colors of "Petals" (showy portion composed of petaloid staminodes):

PMS#186 (Red) with small, irregular splashes of PMS#187. The perianth segments (petals and sepals) are also PMS#186 (Red), but are a reduced pigment intensity and have a glaucous (powdery) coating (grey-white). Due to the unusual composition of the reproductive parts, self pollination is more common in cannas than is cross pollination. The petaloid stamen and style are visible at the center of the flower. The stamen can be recognized by the presence of the single anther-cell along its upper margin. The pistil is made up of the stigma or tip, the petaloid style and a three locular ovary. The ovary is borne on a short pedicel and each loculus contains numerous anatropous ovules attached to an axile placenta. The rarely formed capsule has a warty pericarp that disintegrates at maturity to release the seeds.

*Terminal axis.*—Indeterminate.

*Lateral axis.*—Cymose and determinate.

*Petaloid staminodes.*—PMS#186 (Red).

*Perianth segments.*—PMS#186 (Red) with a reduced pigment intensity and have a glaucous (powdery) coating (grey-white).

*Bud.*—Bud size is 4.3 cm to 6.8 cm comprised of: *Sepal* — 0.5 cm to 1.0 cm. *Petal* — 1.75 cm to 2.85 cm. *Emerging stamenodes — Varying from* 1.5 cm to 4 cm.

Color of reproductive parts:

*Anther.*—Brown (PMS#477 ) to black at dehiscence.

*Stigma.*—Translucent cream to white

*Ovary.*—Green (PMS#371) and burgundy (PMS#490) blend.

*Stamen.*—Dark Red blend, similar to inflorescence.

*Style.*—Blends of dark red.

*Seeds.*—At maturity are oval, near black and approximately 4 mm by 7 mm in size.

Leaves: The alternate leaves are long ovate in shape and have pinnate veins and a dominate mid-rib. They are large, broad, simple, and entire with sheathing petioles. The average size of leaves at maturity is 48 cm in length by 22cm in width. The dominate color in young leaves is burgundy (PMS#490) with green PMS#370 and 371) striations, and burgundy (PMS#490) at maturity.

*Tubers (rhizomes).*—These tuberous rhizomes are a cream-white in color when immature, and transitions into a deep burgundy at maturity. The rhizomes are covered by "papery" scale-like leaves arising at the nodes. This paper-like layering is brown (PMS #439) with darker brown (PMS #440) veining. The average rhizome is 10 cm in length and 2.4 cm in width.

*Root.*—The fleshy roots arise from the internodes of the rhizomes and vary from 1–3 mm in diameter and are an average length of 26.0 cm.

*Flowering time.*—The bloom period begins at approximately twelve (12) weeks after planting (when planted at the recommended season and given reasonable care) and continues until frost. No pruning or pinching is required for optimum flowering performance. Spent blooms are shed quickly (approximately 24 hours after opening).

*Diseases.*—No unusual susceptibility to diseases noted to date.

*Insects.*—No unusual susceptibility to insects noted to date.

GENERAL OBSERVATIONS

*Canna generalis* "Roblibsca" with its dwarf and very compact growth habit is ideal for the smaller garden and landscape designs and the patio/pot culture trend. The burgundy foliage and contrasting scarlet red inflorescence is very striking in the landscape.

For the purpose of ornamental horticulture in our present living environments which include smaller yards and patio gardening, "Roblibsca" is ideal due to several characteristics. These plant characteristics are:

A. Colors of inflorescence and leaves: The carrying power (visibility) of this cultivar's scarlet inflorescence contrast the rich burgundy foliage for a striking landscape display.

B. Dwarf stature: The hybridizer achieved the dwarf height (50–62 cm) of this canna hybrid by serial selection of new cultivars from his breeding program.

C. Compact growth: Another goal was to achieve compact growth habit in a cultivar displaying the striking scarlet red. The achievement of this growth habit is primarily shown by two characteristics: The stem thickness to overall plant height ratio and the internode spacing.
For example: in *Canna generalis* "Roblibsca", the stem thickness (2.3 cm) to average height (60 cm) ratio is 26.09 to 1. In the comparison plant, *Canna generalis* "Red King Humbert", the stem thickness (3.85 cm) to height (158.4 cm) ratio is 41 to 1. The internode spacing of "Red King Humbert" is 26.4 cm and internode spacing of "Roblibsca" is 13.2 cm, creating a more dense, compact overall presentation.
This dwarf and very compact growth habit makes "Roblibsca" ideal for the smaller garden and landscape designs and the patio/pot culture trend.

D. High multiplication rate: For commercial production, plant increase (multiplication rate) is very important. "Roblibsca" increase an average of 10 rhizomes in USDA zone 5 in one season (5 month period) and as high as 25 rhizomes in a USDA zone 9 within one year. This is ideal for production and marketing. Though there are a few cannas of either dwarf stature or adequate multiplication rate, or scarlet inflorescence against burgundy leaves in today's market, applicant is not aware of any that meet all these criteria as completely as does "Roblibsca".

E. Winter Storage: The storage capability of "Roblibsca" is another characteristic that renders this cultivar advantageous both to home gardeners and to commercial growers. The rhizomes are superior for storage because an average of 92% of stored rhizomes are viable after the winter storage period.
The winter storage capability of "Roblibsca" is very important for two reasons. Since cannas are only grown as perennials in USDA zones 90–10 and must be dug and stored in zones 3–8, a vast majority of home gardeners must routinely dig and store the rhizomes during the winter months. There is great variance as to the ability of different varieties to store successfully. "Roblibsca" survives winter storage with a high rate of success. Secondly, this storage ability of "Roblibsca" is of great advantage to commercial canna growers in USDA zones where the cannas must be dug and stored over winter months and a high degree of plant loss renders the product of no marketable value.

COMPARISON TO KNOWN VARIETIES

The cultivar may be compared with known varieties along the following lines.

*Canna generalis* "Red King Humbert" is an appropriate choice for a comparison to *Canna generalis* "Roblibsca"

because of the color combination of its burgundy foliage and red bloom. Though *Canna generalis* "Red King Humbert's" color presentation is similar to "Roblibsca's", "Red King Humbert's" does not meet the current day's demand for a dwarf, compact, dense, landscape canna. *Canna generalis* "Roblibsca", as compared with "Red King Humbert" above, does meet these criteria by being a dwarf, compact, dense landscape canna. In addition, "Roblibsca" sheds its spent blooms much more quickly (18–24 hr.) than "Red King Humbert" (36–48 hr.); thus providing a cleaner and more attractive bloom display.

I claim:

1. A new and distinct cultivar of Canna, substantially as described and illustrated herein, characterized particularly as to novelty by its dwarf height, with overall compact growth characteristics, a multiplication rate of eight to twenty-five plants per growing season, an inflorescence with blooms of scarlet red accented by darker scarlet splashes, contrasting burgundy foliage, and strong winter storage capability providing a cultivar well suited as a garden or pot plant having no unusual susceptibility to the traditional Canna diseases and insects.

* * * * *